(12) United States Patent
Becker et al.

(10) Patent No.: US 8,278,451 B2
(45) Date of Patent: Oct. 2, 2012

(54) PSEUDOAZULENYL NITRONES

(75) Inventors: David A. Becker, Parkland, FL (US); Amolkumar Kolhe, Ann Arbor, MI (US)

(73) Assignee: The Florida International University Board of Trustees, Miami, FL (US)

( * ) Notice: Subject to any disclaimer, the term of this patent is extended or adjusted under 35 U.S.C. 154(b) by 545 days.

(21) Appl. No.: 12/306,246

(22) PCT Filed: Jun. 27, 2007

(86) PCT No.: PCT/US2007/014921
§ 371 (c)(1),
(2), (4) Date: Sep. 28, 2009

(87) PCT Pub. No.: WO2008/002614
PCT Pub. Date: Jan. 3, 2008

(65) Prior Publication Data
US 2010/0016349 A1    Jan. 21, 2010

Related U.S. Application Data

(60) Provisional application No. 60/816,945, filed on Jun. 28, 2006.

(51) Int. Cl.
*C07D 221/04* (2006.01)
*A61K 31/435* (2006.01)

(52) U.S. Cl. ........ 546/112; 546/183; 514/299; 514/456; 549/407

(58) Field of Classification Search .................. 546/112, 546/183; 514/299, 456; 549/407
See application file for complete search history.

(56) References Cited

U.S. PATENT DOCUMENTS

| | | | |
|---|---|---|---|
| 6,083,988 A | 7/2000 | Becker | |
| 6,197,825 B1 | 3/2001 | Becker | |
| 6,291,702 B1 | 9/2001 | Becker | |
| 2004/0152724 A1* | 8/2004 | Dart et al. | 514/310 |

FOREIGN PATENT DOCUMENTS

| | | |
|---|---|---|
| WO | WO-97/19054 | 5/1997 |
| WO | WO-2005/037208 | 4/2005 |

OTHER PUBLICATIONS

Savitz, S. I. "A critical appraisal of the NXY-059 neuroprotection studies for acute stroke: A need for more rigorous testing of neuroprotective agents in animal models of stroke" Experimental Neurology 2007, 205, 20-25.*
Adam, Octavian R. "Symptomatic Treatment of Huntington Disease" Neurotherapeutics: The Journal of the American Society for Experimental NeuroTherapeutics Apr. 2008, vol. 5, 181-197.*
Randolph M. Howes "The Free Radical Fantasy a Panoply of Paradoxes" Annals of the New York Academy of Sciences (2006) 1067: 22-26.*

Anghel et. al. "Antioxidants: not heaven-sent" Harvard Science Review Spring 2010 32-34.*
Becker et al., Stilbazulenyl nitrone (STAZN): A nitronyl-substituted hydrocarbon with the potency of classical phenolic chain-breaking antioxidants. *J. Am. Chem. Soc.* 124: 4678-84 (2002).
Bolli et al., Demonstration of free radical generation in "stunned" myocardium of intact dogs with the use of the spin trap alpha-phenyl N-tert-butyl nitrone. *J. Crit. Invest.* 82: 476-85 (1988).
Brasch et al., Work in progress: methods of contrast enhancement for NMR imaging and potential applications. A subject review. *Radiology.* 147: 781-8 (1983).
Carney et al., Reversal of age-related increase in brain protein oxidation, decrease in enzyme activity, and loss in temporal and spatial memory by chronic administration of the spin-trapping compound N-tert-butyl-alpha-phenylnitrone. *Proc. Natl. Acad. Sci. USA.* 88: 3633-6 (1991).
Chen et al., Oxidative DNA damage and senescence of human diploid fibroblast cells. *Proc. Natl. Acad. Sci. USA.* 92: 4337-41 (1995).
Contestabile et al., Antioxidant strategies for neuro. *Exp. Opin. Ther. Pat.* 11: 573-85 (2001).
Downs et al., Reduction in endotoxin-induced organ dysfunction and cytokine secretion by a cyclic nitrone antioxidant. *Intl. J. Immunopharmacol.* 17: 571-80 (1995).
Doyle et al., Nature's sedative: Isolation and structural elucidation of valtrate from *Centranthus ruber. J. Chem. Ed.* 81: 1486-7 (2004).
Edamatsu et al., The spin-trap N-tert-alpha-phenyl-butylnitrone prolongs the life span of the senescence accelerated mouse. *Biochem. Biophys. Res. Commun.* 211: 847-9 (1995).
Esterbauer et al., The role of vitamin E and carotenoids in preventing oxidation of low density lipoproteins. *Ann. NY Acad. Sci.* 570: 254-67 (1989).
Floyd et al., Free radical damage to protein and DNA: mechanisms involved and relevant observations on brain undergoing oxidative stress. *Ann. Neurol.* 32: S22-7 (1992).
Hensley et al., Amyloid beta-peptide spin trapping. I: Peptide enzyme toxicity is related to free radical spin trap reactivity. *NeuroReport.* 6: 489-92 (1995).
Keana et al., Influence of structure on the reduction of nitroxide MRI contrast-enhancing agents by ascorbate. *Physiol. Chem. Phys. Med. NMR* 16: 477-80 (1984).
Maxwell et al., Anti-oxidant therapy: Does it have a role in the treatment of human disease? *Exp. Opin. Invest. Drugs.* 6: 211-36 (1997).
Oliver et al., Oxidative damage to brain proteins, loss of glutamine synthetase activity, and production of free radicals during ischemia/reperfusion-induced injury to gerbil brain. *Proc. Natl. Acad. Sci USA.* 87: 5144-7 (1990).
Roza et al., Free radicals in pancreatic and cardiac allograft rejection. *Transplant. Proc.* 26: 544-5 (1994).
Sanders et al., Spontaneous oxygen radical production at sites of antigen challenge in allergic subjects. *Am. J. Respir. Crit. Care Med.* 151: 1725-33 (1995).

(Continued)

*Primary Examiner* — David K O'Dell
(74) *Attorney, Agent, or Firm* — Marshall, Gerstein & Borun LLP

(57) ABSTRACT

Disclosed herein are pseudoazulenyl nitrone compounds and methods of using these compounds to trap free radicals and to treat, prevent, or ameliorate various diseases associated with free radicals.

8 Claims, No Drawings

OTHER PUBLICATIONS

Schulz et al., Potassium deprivation-induced apoptosis of cerebellar granule neurons: a sequential requirement for new mRNA and protein synthesis, ICE-like protease activity, and reactive oxygen species. *J. Neurosci.* 16: 4696-706 (1996).

Socci et al., Chronic antioxidant treatment improves the cognitive performance of aged rats. *Brain Res.* 693: 88-91 (1995).

Steinberg et al., Beyond cholesterol. Modifications of low-density lipoprotein that increase its atherogenicity. *N. Engl. J. Med.* 320: 915-24 (1989).

Steinberg, Clinical trials of antioxidants in atherosclerosis: are we doing the right thing? *Lancet.* 346: 36-8 (1995).

Yamashita et al., The effects of alpha-phenyl-tert-butyl nitrone (PBN) on copper-induced rat fulminant hepatitis with jaundice. *Free Radical Biol. Med.* 21: 755-61 (1996).

International Search Report and Written Opinion of the International Searching Authority, European Patent Office, PCT/US2007/014921, dated Dec. 20, 1007.

International Preliminary Report on Patentability, dated Jan. 6, 2009.

* cited by examiner

PSEUDOAZULENYL NITRONES

CROSS REFERENCE TO RELATED APPLICATIONS

This application claims the benefit of U.S. Provisional No. 60/816,945, filed Jun. 28, 2006, which is incorporated by reference in it entirety herein.

BACKGROUND

International Publication No. WO 1997/019054 and corresponding U.S. Pat. Nos. 6,083,988; 6,197,825; and, 6,291,702 disclose certain chromotropic nitrone radical scavenging agents, methods for making these agents, and methods for their use. These compounds are effective in trapping free radicals, and thus have utility as antioxidants in biological systems. Additional information on these and similar compounds was published in Becker et al., *J. Am. Chem. Soc.*, 124:4678-84 (2002).

Radical scavenging is an important method for garnering information on free radicals that are difficult to impossible to detect by direct spectroscopic observation because of their exceedingly short lifetimes and low concentrations. Two classes of radical scavenging agents that have received the most attention are nitroso compounds and nitrones. Of these, nitrones have been used more frequently, especially in biological systems.

The most commonly cited drawbacks of spin trapping agents (or radical scavengers) bearing a nitroso functionality are instability and toxicity. Because of these undesirable characteristics, researchers often use nitrone spin traps despite the fact that their nitroxide spin adducts generally provide less structural information from electron spin resonance (ESR) than adducts from nitroso based spin traps. Furthermore, due primarily to disproportionation, nitroxides obtained from the addition of certain carbon-centered radicals (tertiary alkyl and aryl) to the most widely used nitrone spin traps (alpha-phenyl-N-tert-butylnitrone (PBN), pyridine N-oxide-4-N-tert-butylnitrone (POBN) and dimethylpyrroline N-oxide (DMPO)) are less persistent than those obtained from addition of such radicals to nitroso compounds.

The use of isotopically labeled spin traps or the application of special equipment consisting of GC/MS or HPLC-interfaced ESR spectrometers designed to detect, isolate, and characterize free radical adducts of nitrone spin traps in biological systems have been reported with varied success.

Nitrones behave as spin trapping agents when a diamagnetic nitrone compound (the "spin trap" or "radical scavenger") reacts with a transient free radical species (having the "spin") to provide a relatively more stable radical species (referred to as the "spin adduct"). The spin adduct can be detected by electron paramagnetic resonance (EPR) spectroscopy if the spin adduct has a reasonable lifetime. Thus, information about the spin can be gleaned from a study of the structure and spectroscopic characteristics of the spin adduct.

Various examples of medical applications of radical scavengers are described below.

The toxicity of synthetic β-amyloid peptide preparations toward glutamine synthetase could be correlated with the characteristics of the EPR signal generated by the spin adduct formed from each batch of synthetic β-amyloid peptide and the spin trap PBN. See, Hensley, et al., *NeuroReport* 6:489-492 (1995). β-Amyloid peptides are neurotoxic substances that are postulated to be involved in the etiology of Alzheimer's disease.

Low molecular weight nitroxides are non-immunogenic. Moreover, they are typically cell permeable and can exist as a non-toxic, stable free radical capable of partitioning among various cellular compartments. Being paramagnetic, nitroxides are detectable by EPR spectrometry and may serve as contrast agents in magnetic resonance imaging (MRI). See, Brasch, *Radiology* 147:781 (1983); Keana, et al., *Physiol. Chem. Phys. Med. NMR* 16:477 (1984). Nitroxides have also been used as biophysical markers to probe cellular metabolism, oxygen level, intracellular pH, protein/lipid mobility and membrane structure. Hence, nitroxides find use in a number of diagnostic methods to determine the physiological/medical condition of a subject or the biophysical characteristics of a given sample, including samples obtained from a biological fluid.

Free radicals and oxidative damage have been implicated in brain aging and several neurodegenerative diseases. See, Socci, et al., *Brain Research* 693(1-2):88-91 (1995). Chronic treatment of aged rats with certain compounds, including the spin trapping agent alpha-phenyl N-tert-butylnitrone (PBN) and the antioxidant alpha-tocopherol (vitamin E), was found to benefit (i.e., improve) age-related changes in cognitive performance.

In vitro and in vivo evidence is mounting that the administration of antioxidants can strongly reduce the rate of progression of lesion formation associated with the process of atherosclerosis. Based on several experimental models, including low density lipoprotein (LDL)-receptor-deficient rabbits, cholesterol-fed rabbits and cholesterol-fed non-human primates, several antioxidants have manifested a 50-80% reduction in the rate of progression of lesions. The effectiveness of probucol, butylated hydroxytoluene (BHT), N,N'-diphenylphenylenediamine, and vitamin E are attributed to their respective antioxidant potentials and to the proposition that oxidative modification of LDL contributes to the progression of atherosclerosis. See, Steinberg, *Lancet* 346(8966):36-38 (1995). The one-electron oxidative potentials (vs. NHE) of vitamin E in an aqueous solution at pH 7 and 20° C. is 0.48 V. The oxidative potentials of PBN, POBN, and DMPO range from about 1.5-2.0 V.

Further, Downs, et al., *Int'l J. Immunopharmacol.* 17(7): 571-580 (1995), have shown that a cyclic nitrone antioxidant, MDL 101,002, reduces organ dysfunction and cytokine secretion induced by lipopolysaccharide (LPS) administered to rats. The ability of MDL 101,002 to prevent LPS-induced pulmonary edema, leukopenia and thrombocytopenia was also tested. It was found that MDL 101,002 prevented pulmonary edema and partially reduced thrombocytopenia, but failed to prevent leukopenia. These results were consistent with the role that oxygen free radicals played in the development of endotoxin-induced organ dysfunction and shock. It was suggested that free radical scavengers could reduce the mortality consequent to sepsis by organ dysfunction, at least in part, through a reduction in free radical-stimulated cytokine secretion.

Allergic reactions generate reactive oxygen species, including superoxide anions, which usher the influx of inflammatory cells to the site of allergen challenge and contribute to allergic inflammation. The inflammation may, in turn, lead to cell or tissue injury. For allergic reactions in the lung, these processes are also accompanied by increased vascular permeability and changes in airway mechanics. See, Sanders, et al. *Am. J. Respir. Crit. Care Med.* 151:1725-1733 (1995). Thus, the administration of radical scavenging agents to the site of challenge may reduce the inflammatory response and help reduce tissue or cell damage.

Separately, oxygen-derived free radicals are suspected in playing a role in cytotoxicity during episodes of allograft rejection/destruction following infiltration of the graft by mononuclear cells. The administration of radical scavengers thus may inhibit or reduce the incidence of allograft rejection. See, Roza, et al., *Transplantation Proceedings* 26(2):544-545 (1994).

New reagents that could visually signal the formation of oxidative species would be extremely useful not only in skin tests or in cell culture, but also in determining, for example, the compatibility of a patient's white blood cells with a particular kidney dialysis membrane. In vitro colorimetric assays would be of great utility.

PBN has been shown to offer protection in the cardiovascular disease area, in particular, by trapping free radicals generated during ischemia-reperfision-mediated injury to the heart. See, e.g., Bolli, et al. *J. Clin. Invest.* 82:476 (1988). The benefits of trapping free radicals generated in similar types of injury to the brain of experimental animals has also been demonstrated. See, e.g., Oliver, et al. *Proc. Nat'l. Acad. Sci. USA* 87:5144 (1990); Carney, et al. *Proc. Nat'l. Acad. Sci. USA*. 88:3636 (1991); Floyd. *Science* 254:1597 (1991). Oxidative damage to protein and DNA is mediated by oxygen free radical intermediates, leading to strand breaks and base modifications. Enzymes, such as glutamine synthetase, can also be inactivated by oxidative processes. Such damage can be observed, for example, in animals subjected to brain ischemia/reperfusion injury. See, Floyd, et al. *Ann. Neurol.* 32:S22-S27 (1992).

Evidence is also available that PBN inhibits oxidative modification of cholesterol and triglycerides of low density lipoproteins (LDL). Oxidative modification of LDL, along with lipid peroxidation and free-radical mediated reactions, is a process that is implicated in the initiation of atherosclerosis. See, e.g., Steinberg, et al. *N. Engl. J. Med.* 320:915 (1989); Esterbauer, et al. *Ann. N.Y. Acad. Sci.* 570:254 (1989).

Free radicals and oxidative damage have been proposed as the underlying reasons for aging, chronic and degenerative diseases of aging, and acute clinical conditions. Daily administration by intraperitoneal injection of PBN to an aged animal model showed that PBN offered a remarkable extension of the lifespan in both male and female populations. See, Packer, et al., *Biochem. Biophys. Res. Commun.* 211(3):847-849 (1995). PBN could have prophylatic value against the onset of, at least, pathological senescence.

Ames and co-workers (*Proc. Nat'l. Acad. Sci. USA* 92:4337-4341 (1995)), hypothesized that oxidative DNA damage contributes to replicative cessation in human diploid fibroblast cells. It was found that senescent cells, i.e., those cells that have ceased growth in culture after a finite number of population doublings, excise from DNA four times more 8-oxoguanine per day than early-passage young cells. Also, levels of 8-oxo-2'-deoxyguanosine in DNA of senescent cells are about one third higher than those found in DNA of young cells. Most interestingly, PBN effectively delayed the onset of senescence and rejuvenated near senescent cells, perhaps acting as either an antioxidant or as a radical scavenging agent.

There are several non-medical applications for the use of radical scavengers, such as nitrones. A number of factors influence fat stability and the formation of lipid oxidation products. Increased unsaturation, increased frying time, increased exposure of the oil to air, and increased trace metal content will all result in decreased oxidative stability. The presence of silicones in a frying oil will cause increased oil stability by yet unknown mechanisms. Published data indicates that filtration of oils through certain active adsorbents will increase the useful frying life of an oil during actual fryer use by removal of colored materials, free fatty acids and other oxidation products.

Usually peroxides decompose at about 150° C. Therefore at frying temperatures, the accumulation of peroxides does not occur. Peroxide values usually are a measure of lipid oxidation at lower temperatures such as those used for storage of fats or a product. The relationship between storage time and peroxide value can then be used to measure quality.

The Schall oven test involves simply putting a small amount of the fat into a beaker and placing it into an oven under standardized conditions at 60° C. to oxidize the sample. Samples then are taken and peroxide values determined. There are many other tests available to check frying oil quality, all which purport to inform the operator when to do something with the used fat—either filter it through active filters, discard it, or dilute it with a less degraded fat. Some tests which have been used to check frying oil quality are the saponification color index, 2,6-dichloroindole phenol color test, methylene blue color test, and iodine color scale. These tests allegedly determine when the fat has degraded and can no longer produce a high quality food product. For instance, the Rau test from E. Merck is a colormetric test kit which contains redox indicators that react with total oxidized compounds in a sample. It has a four color scale and is used for diagnoses of fat quality. The fourth color scale indicates a degraded oil and the oil should be discarded. All these tests differ in reliability and may be more tedious to perform than necessary.

Surprising difficulty in starting a lawn mower, trail bike, outboard motor, or similar infrequently used gasoline engine, is caused by "bad" petroleum. Petroleum is subject to autoxidation, like oils in foods and in the human body. When gasoline is left for any long period (e.g., a few months or more), gums are formed by the reaction of oxygen with unsaturated components of the fuel. BHT (also known as 2,6-di-tert-butyl p-cresol) is a U.S. government approved gasoline additive that meets military requirements for gasoline stability. A half pound of BHT added to 1,100 gallons of gasoline prevents gum formation when gasoline was stored in sealed (with standard rubber washers) 5-gallon cans for periods up to two years in the Mojave desert in fill sunlight, compared to a storage life of only a few months for unprotected gasoline. The amount currently recommended for military use is 1 pound BHT to 1,100 gallons of gasoline. For even longer storage, BHT, alone, may not be sufficient to prevent spoiling of the fuel.

Other materials that are affected by similar aging mechanisms include plastics, rubber, paint asphalt, roofing shingles, oils and lubricants.

Accordingly, radical scavengers exhibit a wide range of properties that are applicable to many end uses. There exists a continuing need to discover new, effective substances exhibiting free radical/spin trapping and/or antioxidant activity which are potentially useful for a wide range of analytical preservative, diagnostic, prophylactic and therapeutic applications.

SUMMARY

Disclosed herein are a novel set of radical scavenging compounds, which can be useful in a number of applications, including ameliorating various diseases associated with the presence of radicals and as fuel preservatives.

Thus, one aspect provides pseudoazulenyl nitrones having a structure according to formula (I) or (II):

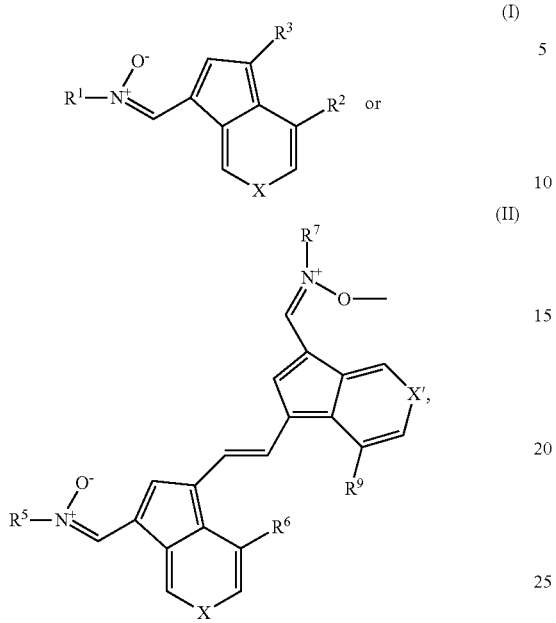

wherein $R^1$, $R^5$, and $R^7$ are the same or different and are independently selected from the group consisting of hydrogen, $C_{1-4}$ alkyl, phenyl, substituted phenyl, benzyl, substituted benzyl, tris(3-hydroxypropyl)methyl, (3-carboxy-1,1-dimethyl)propyl, and 3-sulfonatophenyl; $R^2$, $R^6$, and $R^9$ are the same or different and are selected from the group consisting of hydrogen, $C=C(H)N^+(R^1)O^-$, $C_{1-10}$alkyleneOC(O)$C_{1-10}$alkyl, and CHO; $R^3$ is selected from the group consisting of hydrogen, $C_{1-22}$alkyl, $SR^{12}$, and $SO_3^-$; X is selected from the group consisting of O, S, and $NR^4$; X' is selected from the group consisting of O, S, and $NR^8$; $R^4$ and $R^8$ are the same or different and are selected from the group consisting of hydrogen, $C_{1-22}$alkyl, phenyl, substituted phenyl, $(C_{1-22}$alkyleneN$(R^{12})_2^+)_n C_{1-22}$alkyleneN$(R^{12})_2$, $C_{1-22}$alkyleneOR$^{11}$, $C_{1-22}$alkyleneP$(R^1)_3^+$, $C_{1-22}$alkylene aryl, $C_{1-22}$alkylene substituted aryl, $C_{1-22}$alkylene heteroaryl, and $C_{1-22}$alkylene substituted heteroaryl; $R^{10}$ is independently selected from the group consisting of hydrogen, $C_{1-10}$alkyl, $C_{1-10}$alkyleneN$(R^{12})_3^+$, and $C_{1-10}$alkylene-$C_6H_4$—$C_{1-10}$alkyleneN$(R^{12})_3^+$; $R^{11}$ is selected from the group consisting of hydrogen, $C_{1-10}$alkyl, $SO_2CF_3$, $SO_2CH_3$, $SO_2C_6H_4CH_3$, and $SO_2C_4F_9$; and $R^{12}$ is selected from the group consisting of hydrogen, $C_{1-22}$alkyl, aryl, heteroaryl, substituted aryl, and substituted heteroaryl; n is an integer from 0 to 3; or a pharmaceutically acceptable salt thereof.

In some embodiments, the compound of formula (I) or (II) is

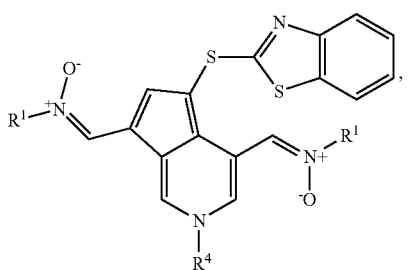

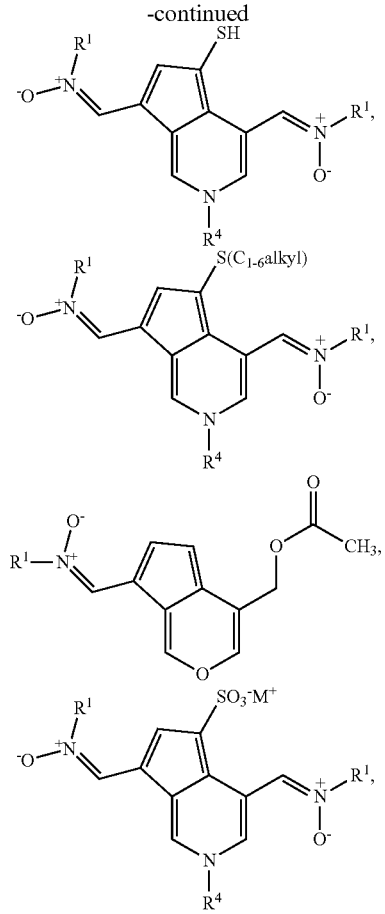

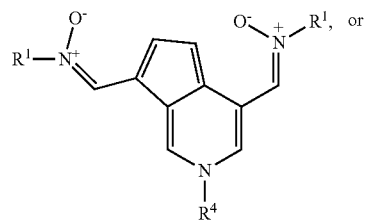

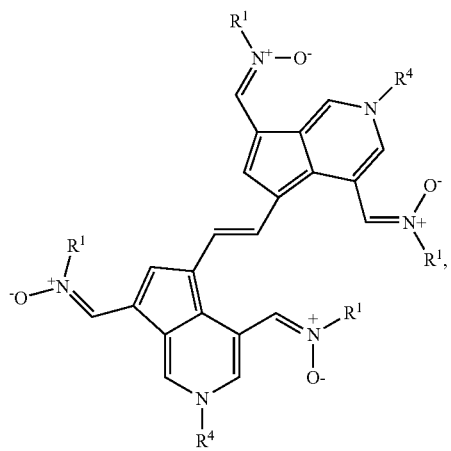

wherein M is selected from the group consisting of Li, Na, K, and Cs.

Specific compounds of formula (I) or (II) include, but are not limited to,

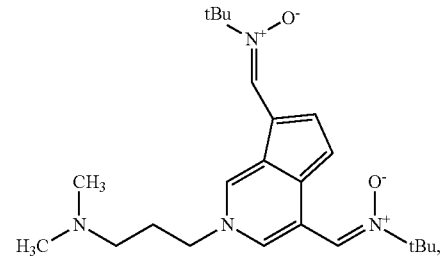

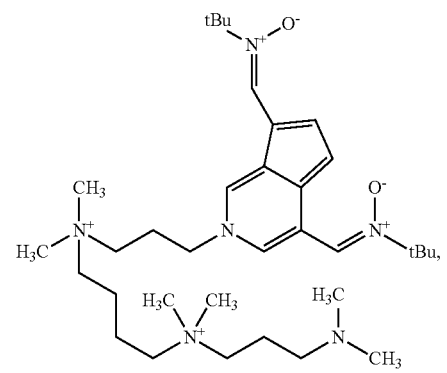

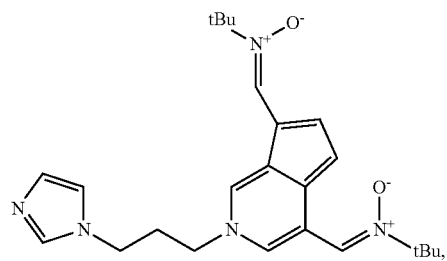

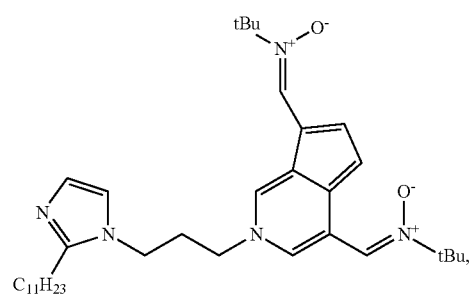

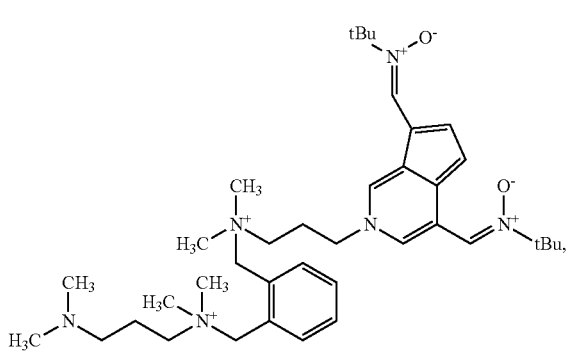

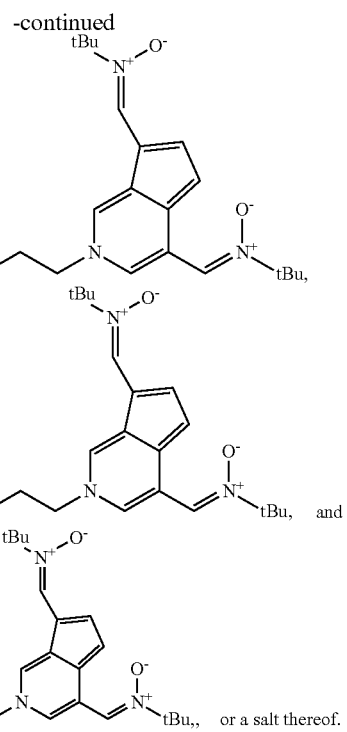

or a salt thereof.

Another aspect provides methods of trapping a reactive free radical comprising contacting a compound as disclosed herein with the reactive free radical and allowing said compound to combine with the reactive free radical to provide an adduct of the compound and the reactive free radical.

Yet another aspect provides a method of alleviating a pathological condition mediated or initiated by a reactive free radical comprising administering an effective amount of a compound as disclosed herein in a pharmaceutically acceptable carrier to a subject in need thereof. In some embodiments, the pathological condition is selected from the group consisting of ischemia, reperfusion injury, head trauma, brain trauma, acute respiratory distress syndrome, neurological disorder, Alzheimer's disease, stroke, Parkinson's disease, Huntington's disease, Lou Gehrig's disease, Wilson's disease, aging, senescence, apoptosis, and inflammation.

Still another aspect provides a method of screening for free radicals comprising contacting a compound suspected of producing free radicals with a compound as disclosed herein to form an adduct of the free radical and the compound as disclosed herein, and measuring a ratio of the adduct to the compound as disclosed herein, wherein a ratio greater than 0 indicates the presence of free radicals.

DETAILED DESCRIPTION

A new series of azulenyl-type nitrones, termed "pseudoazulenyl" nitrones, has been developed. The compounds and methods of synthesizing and using the compounds are disclosed below.

Of particular importance regarding radical scavenging with the pseudoazulenyl nitrones of the present invention is their capacity to tag free radicals by yielding characteristically colored and highly visible diamagnetic (and paramagnetic) spin adducts. Thus, the present nitrones provide the potential to implicate the intermediacy of, and establish the identity of, free radicals in situations where presently available ESR detection/isolation technology may fail.

Although considerably more persistent than most free radicals, nitroxides are nevertheless often subject to the usual free radical destruction processes of combination, disproportionation, and oxidation/reduction, yielding diamagnetic products. The rapid formation of diamagnetic spin adducts in traditional spin trapping experiments is an unwanted occurrence which can constitute a serious obstacle, because once such products are formed in biological systems employing conventional nitrone spin traps, they are lost among a vast number of diverse diamagnetic molecules.

The ability to easily locate diamagnetic spin adducts in complex mixtures offers an appealing alternative when faced with technical difficulties often encountered in attempting to isolate nitroxides resulting from conventional nitrone spin traps before they decay into diamagnetic species. In radical scavenging using the compounds of the present invention, the characteristic chromophore of the diamagnetic spin adducts arising from nitroxides via combination, disproportionation, or reduction, while different from the chromophore of the azulenyl nitrone, is in fact the same as that of the initially formed ESR-detectable nitroxide spin adducts. Therefore, this characteristic chromophore should also expedite the purification (and subsequent structure determination) of these paramagnetic species from reaction mixtures amenable to nitroxide longevity.

Even though nitroxides possess a visible chromophore of their own, their characteristic red color is due to an absorption with a very low extinction coefficient centered around 460 nm. For example, the visible absorption spectrum in hexane for di-t-butylnitroxide shows a maximum at 465 nm with log e=0.95. The extinction coefficient for the absorption giving rise to the color of the diamagnetic azulene-containing spin adducts described herein is between one to two orders of magnitude greater. See, Smith, P. A. S. *Open-Chain Nitrogen Compounds*, W. A. Benjamin, Inc., New York, 1965, Vol. 2, p. 105, and references cited therein for additional discussions on nitroxide absorption spectra.

Pseudoazulenyl nitrones of the present invention are compounds of general structural formula (I) or (II):

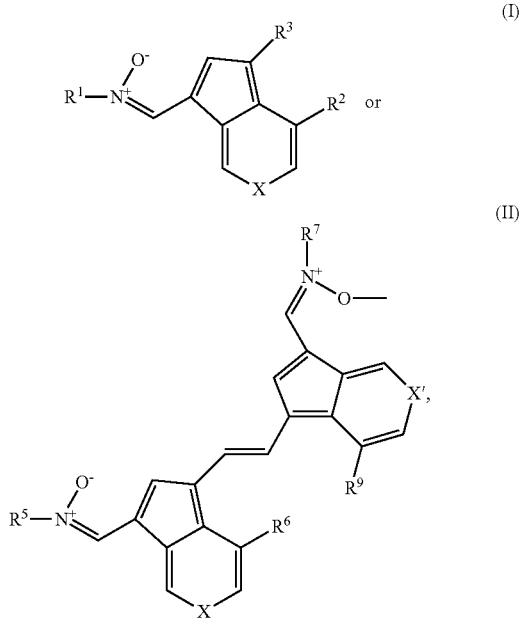

wherein $R^1$, $R^5$, and $R^7$ are the same or different and are independently selected from the group consisting of hydrogen, $C_{1-4}$ alkyl, phenyl, substituted phenyl, benzyl, substituted benzyl, tris(3-hydroxypropyl)methyl, (3-carboxy-1,1-dimethyl)propyl, and 3-sulfonatophenyl; $R^2$, $R^6$, and $R^9$ are the same or different and are selected from the group consisting of hydrogen, C=C(H)N$^+$(R$^1$)O$^-$, $C_{1-22}$alkyl, $C_{1-10}$alkyleneOC(O)$C_{1-10}$alkyl, and CHO; $R^3$ is selected from the group consisting of hydrogen, $C_{1-22}$alkyl, $SR^{12}$, and $SO_3^-$; X is selected from the group consisting of O, S, and $NR^4$; X' is selected from the group consisting of O, S, and $NR^8$; $R^4$ and $R^8$ are the same or different and are selected from the group consisting of hydrogen, $C_{1-22}$ alkyl, phenyl, substituted phenyl, $(C_{1-22}alkyleneN(R^{12})_3^+)_nC_{1-22}alkyleneN(R^{12})_2$, $C_{1-22}alkyleneOR^{11}$, $C_{1-22}alkyleneP(R^1)_3^+$, $C_{1-22}$alkylene aryl, $C_{1-22}$alkylene substituted aryl, $C_{1-22}$alkylene heteroaryl, and $C_{1-22}$alkylene substituted heteroaryl; $R^{10}$ is independently selected from the group consisting of hydrogen, $C_{1-10}$alkyl, $C_{1-10}alkyleneN(R^{10})_3^+$, and $C_{1-10}$alkylene-$C_6H_4$—$C_{1-10}alkyleneN(R^{12})_3^+$; $R^{11}$ is selected from the group consisting of hydrogen, $C_{1-10}$alkyl, $SO_2CF_3$, $SO_2CH_3$, $SO_2C_6H_4CH_3$, and $SO_2C_4F_9$; and $R^{12}$ is selected from the group consisting of hydrogen, $C_{1-22}$alkyl, aryl, heteroaryl, substituted aryl, and substituted heteroaryl; n is an integer from 0 to 3; or a pharmaceutically acceptable salt thereof.

The term "aryl" as used herein refers to a monocyclic or polycyclic aromatic group, preferably a monocyclic or bicyclic aromatic group, e.g., phenyl or naphthyl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. Also contemplated are aryl groups which are highly colored, and can act as dyes. Representative examples of such groups include those disclosed in *Conn's Biological Stains, A Handbook of Dyes, Stains and Fluorochromes for Use in Biology and Medicine,* 10th ed. Some examples include, but are not limited to, rhodamine 110, and esters thereof. In a specific embodiment, the rhodamine 110 is attached to the compound of formula (I) or (II) via a ester linkage with a pendant hydroxyl group, e.g., wherein $NR^4$ comprise $C_{1-10}$alkyleneOaryl, and aryl comprises rhodamine 110.

The term "heteroaryl" as used herein refers to a monocyclic or bicyclic ring system containing one or two aromatic rings and containing at least one nitrogen, oxygen, or sulfur atom in an aromatic ring. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkylene" as used herein refers to an alkyl group having a substituent. For example, the term "alkylene heteroaryl" refers to an alkyl group substituted with a heteroaryl group. The alkylene group is optionally substituted with one or more substituent previously listed as an optional alkyl substituent.

The terms "substituted aryl" and "substituted heteroaryl," e.g., "substituted phenyl," as used herein refer to an aryl or heteroaryl group substituted by a replacement of one, two, or three of the hydrogen atoms thereon with a substitute such as halo, OR', N(R')$_2$, C(=O)N(R')$_2$, CN, nitro, nitroso, alkylcarbonyl, alkoxycarbonyl, carboxylate, alkyl, substituted alkyl, aryl, substituted aryl, heteroaryl, substituted heteroaryl, cycloalkyl, substituted cycloalkyl, heterocycloalkyl, substituted heterocycloalkyl, O(CH$_2$)$_{1-3}$N(R')$_2$, O(CH$_2$)$_{1-3}$CO$_2$H, and trifluoromethyl. R' of the formulas: OR', N(R')$_2$, C(=O)N(R')$_2$ and O(CH$_2$)$_{1-3}$N(R')$_2$ can be hydrogen or $C_{1-8}$alkyl.

Some specific compounds of formula (I) or (II) contemplated include:

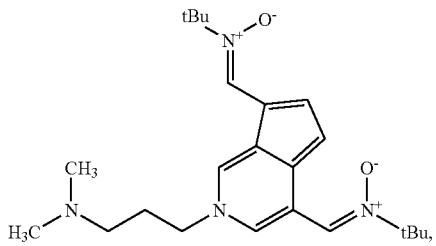
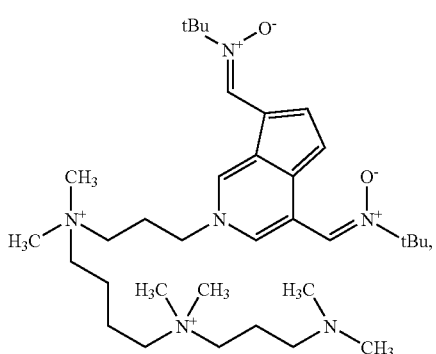
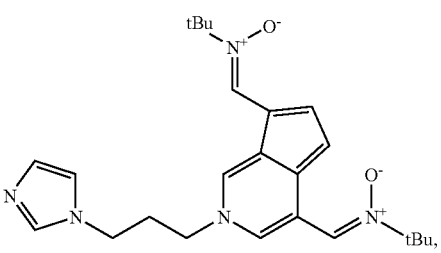
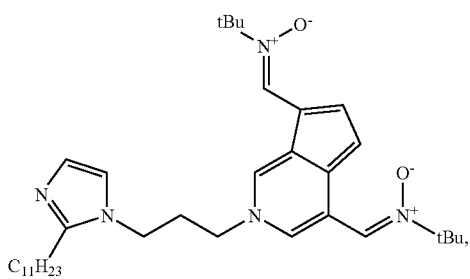
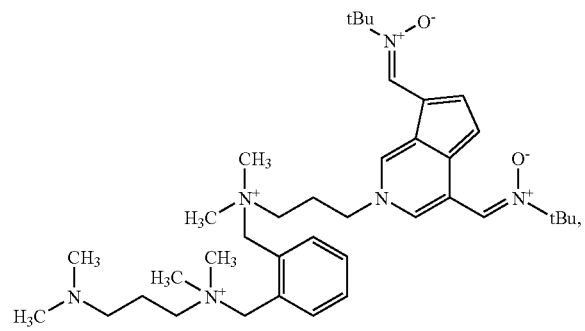

-continued

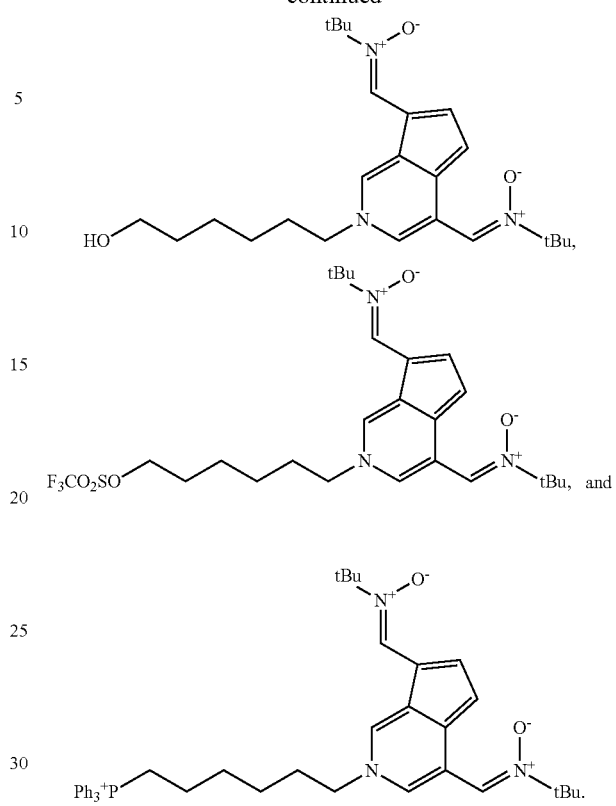

A method of synthesizing a compound of formula (I), when X=O, begins with valtrate, which is isolated from the roots of the plant *centranthus ruber* (Red Valerian) according to the procedure in Doyle et al., *J. Chem. Ed.* 81:1486 (2004). Valrate is treated with an acid, such as trifluoroacetic acid, to form baldrinal, reported in Thies, *Tetrahedron*, 24:313 (1968). Baldrinal is subsequently reacted with a hydroxylamine to form a compound of formula (I). This synthetic pathway is shown in the following scheme.

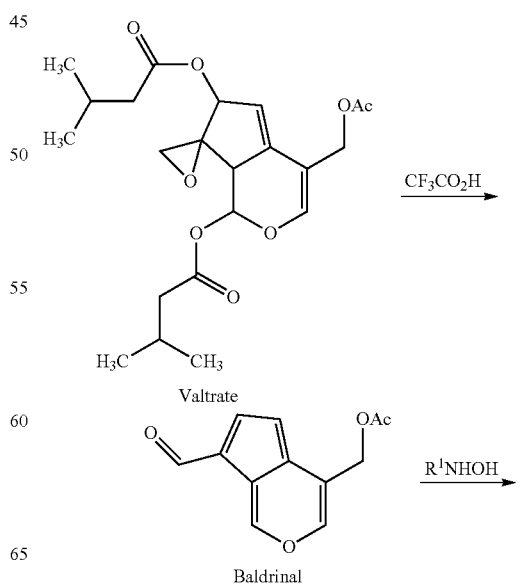

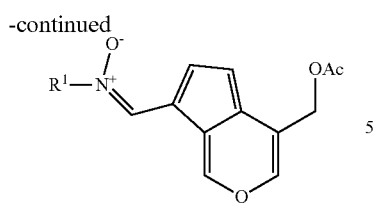

Alternatively, when baldrinal is reacted with a primary amine (e.g., R⁴NH₂) according to the procedure of Seitz et al., *Arch. Pharm.*, 318:946 (1985), intermediate (III) is formed, which can be transformed into compounds of formula (I), where X=NR⁴. The synthesis is outlined in the following scheme.

In other embodiments, intermediate (III) can be reacted under a variety of conditions to further modify the structure, prior to formation of the nitrone functional group. Deprotection of the acetate to form a hydroxyl group allows access to a large number of alternative functional groups. For example, upon treatment with an aryl or heteroaryl disulfide reagent, under conditions reported in Porshnev et al., *Khim. Geterotsiktich Soedinenii*, 1278 (1977), an aryl thiol ether (IV) is synthesized.

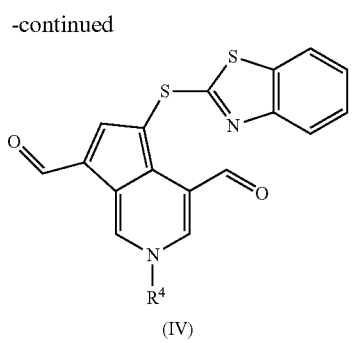

The substituents of this aryl thiol ether (IV) can be transformed into a variety of other moieties, nonlimiting examples of which are outlined in the following scheme.

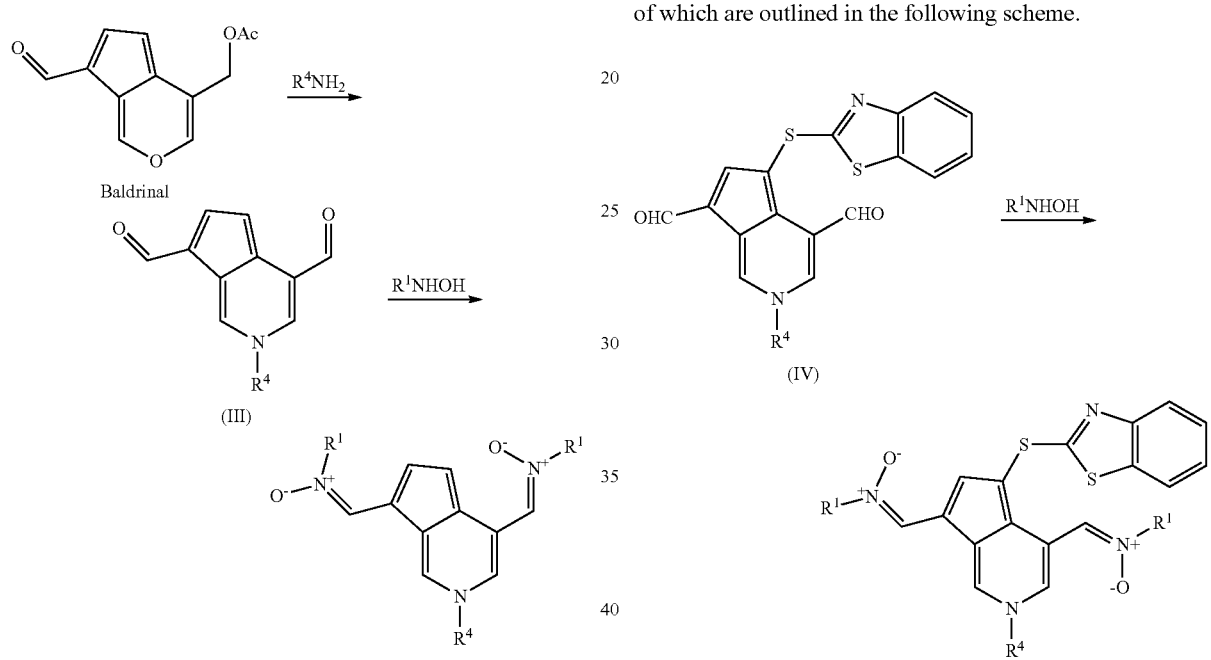

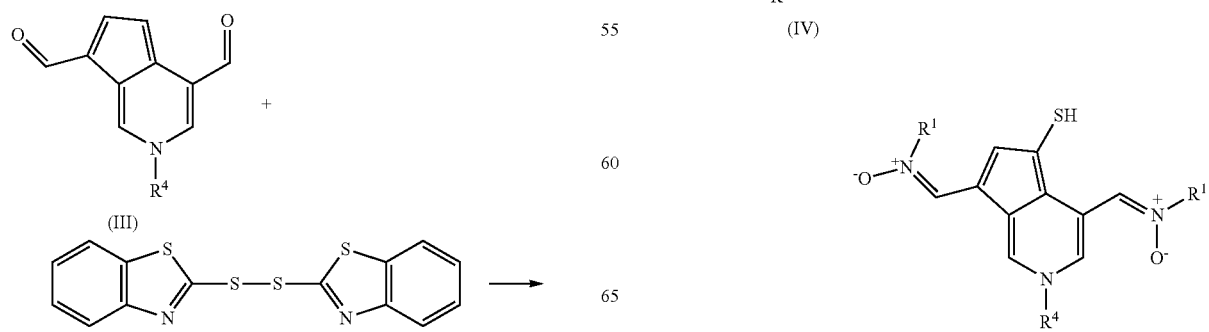

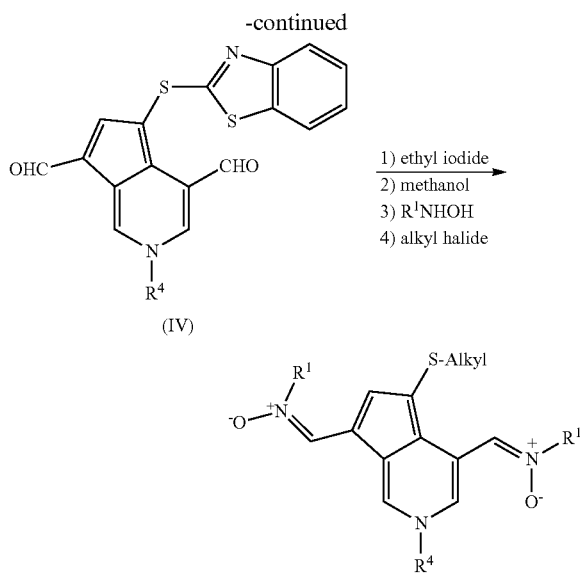

Other nonlimiting transformations for intermediate (III) are shown in the following schemes.

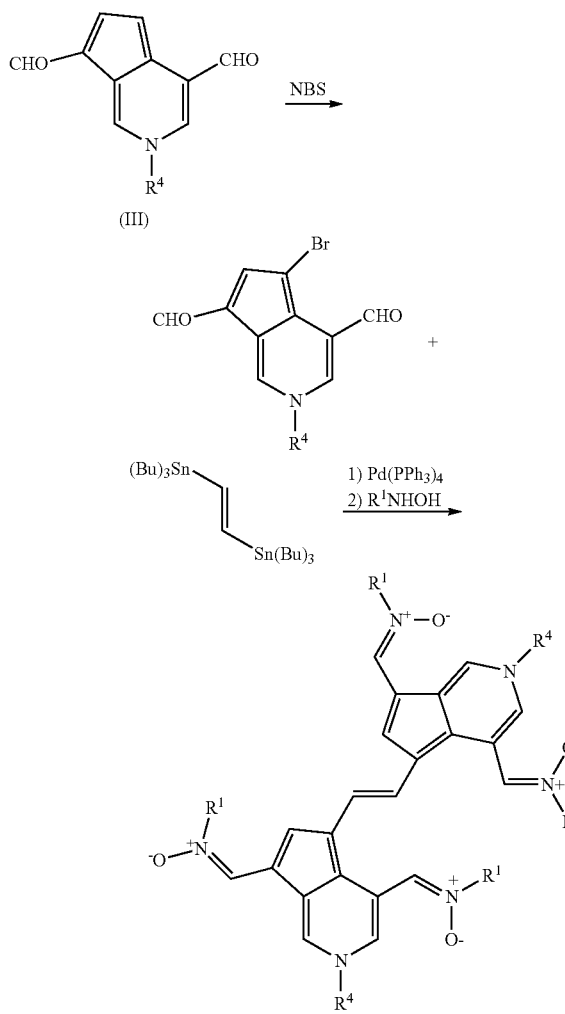

The compounds disclosed herein can be used in a method to trap a reactive free radical. The method comprises contacting the compound with a reactive free radical to provide an adduct comprising the free radical and the compound. The compounds can also be used in a method of detecting oxidation products in a medium comprising contacting the compound with a medium and detecting the presence of an adduct, or an end-product thereof in the resulting mixture. Yet another method contemplated is a method of alleviating the ill effects of a pathologic condition mediated or initiated by a reactive free radical comprising administering an effective amount of a compound of the invention to a subject in need thereof. Still other methods include, but are not limited to, methods of alleviating, ameliorating, treating, preventing, managing, or inhibiting the negative effects of ischemia, reperfusion injury, trauma (particularly head or brain trauma), acute respiratory distress syndrome, neurological (especially cerebral) disorders, Alzheimer's disease, stroke, Parkinson's disease, Huntington's disease, Lou Gehrig's disease, Wilson's disease, aging, senescence, apoptosis, inflammation and the like.

Pseudoazulenyl nitrones are detectable by UV/VIS spectroscopy and HPLC. Upon reaction with free radicals and subsequent decomposition of the adduct, the nitrones generate the corresponding pseudoazulenyl aldehydes. Such aldehydes arise from the decomposition of radical scavengers formed with oxygen-centered free radicals. The aldehydes are, in turn, also detectable by UV/VIS spectroscopy. One can take advantage of the ability to detect the aldehyde to determine the amount of radicals in a subject. Thus, when a subject is dosed with nitrones and subsequently treated in some fashion (e.g., ischemia and/or reperfusion) to cause the formation of free radicals in some part of the subjects anatomy, the amount of free radicals induced in the subject can be gauged by measuring the amount of aldehyde produced. The nitrone is recovered unchanged if no oxidation reaction takes place. The aldehyde to nitrone ratio can be determined in the subject's biological fluids and/or tissue samples (e.g., in the blood, cerebral, or cardiovascular tissue). In this fashion, pseudoazulenyl nitrones are used to gauge the relative levels of reactive free radical production in various locations and/or fluids of the subject. Such analytical techniques can also demonstrate that the pseudoazulenyl nitrones of the present invention are able to penetrate certain barriers that are present in the animal or human anatomy, such as the blood-brain barrier, or whether these compounds prefer to remain or localize in certain tissues (e.g., hippocampus) or fluids (e.g., plasma) after different modes of administration, e.g., intravenous, intraperitoneal, orally, topical, intramucal, opthalmic, and the like.

Because pseudoazulenyl nitrones react with free radicals, physiological events and/or pathological conditions that lead to the formation of free radicals and which thereby having the subject suffer from such event or condition, can be prevented, inhibited, or alleviated by the administration of pseudoazulenyl nitrones. For example, a method of determining the effectiveness of pseudoazulenyl nitrones as a neuro- or cerebroprotectant involves the administration of pseudoazulenyl nitrones to test animals, including rodents, such as gerbils or mice. An ischemic episode then is induced in the test animal. For example, a useful stroke model is provided by subjecting the test animal to a bilateral carotid occlusion (BCO), which reduces the flow of blood to the brain and can result in brain damage and/or tissue infarction. The blood and brains of the BCO-treated rodents are analyzed to determine the relative amounts of pseudoazulenyl nitrone and aldehyde. The ratio of the aldehyde to nitrone concentrations is compared to that found in sham rodents, which were not subjected to one of the oxygen free radical producing procedure. The results indicate that the ratio is higher (i.e., that more aldehyde is observed) in the test rodents versus the sham rodents, indicating that the administration of pseudoazulenyl nitrones to these rodents proceeds to a redox reaction/combination, which affords the aldehyde end product.

The protective effects of pseudoazulenyl nitrones are investigated by subjecting a cell culture to compounds known to induce death in the cells. The nitrone is administered in varying doses to determine the amount needed to inhibit or prevent cell death. By this method, the efficacy of pseudoazulenyl nitrones is determined. As an example, cerebella granular cells (neuronal cells) are treated with a sublethal dose of a toxic agent, e.g., cis-platin, buthionine sulfoximine, or peroxynitrite. The nitrone is either added prior to or after treatment with the toxic agent.

The effective dose of the pseudoazulenyl nitrone is determined using such cell culture assays. The dose typically is about 1 nM to about 100 mM, and can be about 10 nM to about 100 nM, about 150 nM to about 300 nM, about 350 nM to about 500 nM, about 550 nM to about 800 nM, about 0.9 mM to about 1.2 mM, about 1.5 mM to about 3 mM, about 3.5 mM to about 7 mM, about 8 mM to about 10 mM, about 11 mM to about 15 mM, about 16 mM to about 30 mM, about 31 mM to about 50 mM, or about 51 mM to about 100 mM.

The pseudoazulenyl nitrones of the invention, when added to cell cultures, particularly prokaryotic, eukaryotic, and especially mammalian cells, extend the period of cell viability relative to a control cell culture that received no pseudoazulenyl nitrone. Hence, the compounds and methods of the invention inhibit cell apoptosis. (See, e.g., Schulz, J. B. et al., *J. Neuroscience* 16:4696-4706 (1996)). Similar results are obtained with a variety of neuroprotective cell toxicity assays.

The protective effect of pseudoazulenyl nitrones on the formation of oxidative damage in liver DNA and on lipid peroxidation can be determined by by experiments using Long-Evans Cinnamon (LEC) rats. See, e.g., Yamashita, T. et al., *Free Radical Bio. & Med.* 21:755-761 (1996). These rats belong to a new mutant strain with hereditary hepatitis and are used as models for treating Wilson's disease. LEC rats die of fulminant hepatitis within about a week of the development of severe jaundice without intervention. These rats can be used to determined the effect of the pseudoazulenyl nitrone as disclosed herein on radicals implicated in various liver diseases.

The present invention contemplates compositions comprising the pseudoazulenyl nitrone compounds disclosed herein. Preferably, these compositions include pharmaceutical compositions comprising a therapeutically effective amount of a pseudoazulenyl nitrone compound along with a pharmaceutically acceptable carrier.

As used herein, the term "pharmaceutically acceptable" carrier means a non-toxic, inert solid, semi-solid liquid filler, diluent, encapsulating material or formulation auxiliary of any type. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and conventional antioxidants can also be present in the composition, according to the judgement of the formulator. Examples of pharmaceutically acceptable conventional antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like: and the metal chelating agents such as citric acid, ethylenediamine tetraacetic acid (EDTA), sorbitol, tartaric acid, phosphoric acid and the like.

By a "therapeutically effective amount" of a pseudoazulenyl nitrone compound is meant a sufficient amount of the compound to alleviate, modulate, or inhibit the negative or otherwise ill effects of free radical species and/or associated medical disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the medical disorder being treated and the severity of the medical disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The total daily dose of the pseudoazulenyl nitrone compounds of the present invention administered to a human subject in single or in divided doses can be in amounts, for example, from 0.01 to 35 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the compound(s) of this invention per day in multiple doses or in a single dose of from 1 mg, 5 mg, 10 mg, 100 mg, 500 mg or 1000 mg. A submilligram dose may also be appropriate, namely, about 0.1-0.9 mg, preferably, about 0.3, about 0.5, or about 0.7 mg.

The compounds of the present invention may be administered alone or in combination or in concurrent therapy with other agents that exhibit antioxidant activity, such as PBN.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents, emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a therapeutic agent, it is often desirable to slow the absorption of a therapeutic agent from subcutaneous or intramuscular injection. The most common way to accomplish this is to inject a suspension of crystalline or amorphous material with poor water solubility. The rate of absorption of the therapeutic agent becomes dependent on the rate of dissolution of the therapeutic agent which is, in turn, dependent on the physical state of the therapeutic agent, for example, the crystal size and the crystalline form. Another approach to delaying absorption of a therapeutic agent is to administer the therapeutic agent as a solution or suspension in oil.

Injectable depot forms can also be made by forming microcapsule matrices of therapeutic agent and biodegradable polymers such as polylactide-polyalycoside. Depending on the ratio of therapeutic agent to polymer and the composition of the polymer, the rate of therapeutic agent release can be controlled. Examples of other biodegradable polymers include poly-orthoesters and polyanhydrides. The depot injectables can also be made by entrapping the therapeutic agent in liposomes or microemulsions which are compatible with body tissues.

Suppositories for rectal administration of the therapeutic agent can be prepared by mixing the therapeutic agent with a suitable nonirritating excipient such as cocoa butter and polyethylene glycol which are solid at ordinary temperature but liquid at the rectal temperature and will, therefore, melt in the rectum and release the therapeutic agent.

Solid dosage forms for oral administration may include capsules, tablets, pills, powders, prills and granules. In such solid dosage forms the active radical scavenging compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active nitrone compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a nitrone compound of this invention, for either therapeutic or cosmetic applications, further include ointments, pastes, creams, lotions, gels, powders, solutions, sprays, inhalants (e.g., through the oral cavity or intranasally) or patches. The active nitrone component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active nitrone compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Accordingly, the present invention is useful in the treatment or alleviation of disease, especially those disorders related to oxidized species, free radicals, or products of oxidation, including products of polymorphonuclear leukocyte oxidative burst. Such medical conditions may be characterized by inflammation, rheumatoid arthritis, autoimmune disease, flu-like symptoms, decreased cognitive ability, cardiovascular disease, atherosclerosis, respiratory discomfort and the like, which can be reduced by the administration of an effective amount of the pseudoazulenyl nitrone compounds of the present invention.

Reactive free radicals in living tissue are believed to promote heart disease, cancer, Alzheimer's disease, Parkinson's disease, amyotrophic lateral sclerosis (or ALS), rheumatoid arthritis and even antineoplastic (anticancer, antitumor) induced cardiotoxicity. There exist many mechanisms that induce the formation of free radicals in living organisms. Some occur naturally, such as through the metabolic process, while others are introduced into the body by way of chemical agents, radiation, microbes and viruses.

The initial presence of the free radical initiates a chain reaction in which a number of biomolecules in the organism are oxidized. By oxidizing lipids, for example, these free radicals can affect cell membranes, the permeability of cell membranes, ion channels contained therein, cell function, and the like. By oxidizing proteins, for example, free radicals can alter enzymes, muscular function, nerves, and the like. And by oxidizing nucleic acids, for example, free radicals can affect DNA, RNA, and consequently their function, regulation, or expression products. Radical scavenging agents are utilized to terminate or inhibit this damaging cascade of reactions. It has been found that oxygen-centered free radicals and carbon-, nitrogen-, phosphorous- and sulfur-centered radicals react more readily with the radical scavenging agent of the invention than with the potential target biomolecules. The reaction with the radical scavenging agent results in the formation of a stable spin adduct and thus, terminates and/or inhibits the damaging chain reaction.

Therefore, the pseudoazulenyl nitrone compounds of the present invention can be used in a method of treating, alleviating, modulating, or inhibiting the effects in the heart or brain of ischemia or reperfusion injury, acute respiratory distress syndrome (ARDS), sepsis, septic shock and the like. The invention also demonstrates a capacity to preserve organs prior to transplantation comprising contacting the organ to be preserved with an organ preserving effective amount of a compound of the invention.

The phrase "pharmaceutically acceptable salt" includes any type of salt of the pseudoazulenyl nitrones of the present invention, whether derived from the addition to the nitrone of a base or an acid, which is suitable for pharmacologic use. Hence, the salt can be obtained by the addition of a alkali or alkaline earth substance (e.g., sodium hydroxide, calcium carbonate, magnesium sulfate and the like) to a nitrone bearing an acidic group (e.g., carboxylic acid or sulfonic acid). Conversely, any free basic functional groups (such as an amino group) on the nitrone can be treated with an acidic substance (e.g., hydrochloric acid, nitric acid and the like) to provide an acid addition salt.

The compounds of the invention can be administered alone or in combination with one or more other biologically active (preferably, therapeutically active) agents, either substantially simultaneously or sequentially. An effective amount of pseudoazulenyl nitrone, co-administered with a second agent exhibiting some tissue necrosis or toxicity, may reduce the harmful side effect of the co-administered drug while still deriving the benefit of the therapeutic effect of the second drug. Hence, a combination comprising a therapeutically effective amount of adriamycin, taxol, cis-platin, or other anticancer agents, or AZT, DDI, or other protease inhibitors and an amount of pseudoazulenyl nitrone effective to reduce toxicity associated with the other drug(s) is expressly contemplated.

In yet another method, pseudoazulenyl nitrone compounds can be used in the screening of natural products that readily give rise to free radicals, e.g., enediyne antibiotics, such as bleomycin, or iron-centered drugs, which may eventually bind DNA/RNA.

Specific compositions include, but are not limited to, a pharmaceutical composition for alleviating a the ill effects of a pathologic condition mediated or initiated by a reactive free radical, in which the composition comprises an effective amount of the compound of the general formula and a pharmaceutically acceptable carrier. Other compositions comprising the compounds of the present invention and a carrier are also contemplated including, but not limited to, those that inhibit oxidation, a fuel additive, a food additive (such as one that is added to a vegetable oil), a cosmetic (such as a facial or body sunscreen of characteristic colors and which change color, indicating overexposure to oxidative conditions or elements). Still other compositions may be those that alleviate the ill effects of aging and in which the carrier is sterile.

Another contemplated method for use of the compounds of the present invention is one of alleviating the ill effects of ischemia or reperfusion injury in a subject comprising administering to the subject an effective amount of a compound of the invention, a method of alleviating the ill effects of Acute Respiratory Distress Syndrome (ARDS) in a subject comprising administering to the subject an effective amount of a compound of the invention, or a method of alleviating the ill effects of aging, apoptosis, or senescence in a subject comprising administering to the subject an effective amount of a compound of the invention.

The present invention also contemplates a composition for the treatment of an inflammation in a warm-blooded animal comprising a pseudoazulenyl nitrone of the invention a topical carrier. The composition of may come in the form of an aqueous solution, oil, cream, cake, powder, emulsion, or suspension.

EXAMPLES

Extraction of Valtrate (1): Finely grounded root of *centranthus ruber* (Red Valerian) (100 g) was stirred in 800 mL of ethanol for 15 minute. Crude valtrate was obtained after filtration. After column chromatography with 8:2 hexane:ethyl acetate as the solvent system, 9.2 g of valtrate (1) was obtained.

Synthesis of Baldrinal (2): Valtrate (1) (9.2 g) was dissolved in 20 ml of chloroform at room temperature. In another flask, 20 g of trifluoroacetic acid was dissolved in 40 ml of chloroform. This second solution then was added to the first solution. The clear solution became dark green/blue after stirring for 5 minutes. Chloroform (60 ml) was added to the reaction mixture, and the reaction mixture was washed with water until a pH of 4 was reached. Sodium chloride with 0.5% $NaHCO_3$ (125 mL) was added to neutralize the mixture. Baldrinal (2, 1.1 g) was collected as a yellow liquid using column chromatography with 8:2 hexanes:ethyl acetate as solvent.

Synthesis of Cyclopenta[c]pyridine (3): Baldrinal (2) (1.1 g) was reacted with 2.5 g of sec-butylamine. After stirring for 10 minutes at room temperature, color changes from yellow to orange. When all the baldrinal was reacted, the excess amine was removed by rotary evaporation. After column chromatography with 8:3 hexanes:ethyl acetate as solvent, 15.7 mg of cyclopenta[c]pyridine (3) was collected.

Synthesis of Dinitrone cyclopenta[c]pyridine (4): Cyclopenta[c]pyridine (3) was mixed with 34.4 mg of N-tert-butyl hydroxylamine and 33 mg of $MgSO_4$ followed by 2 ml of pyridine. The flask was flushed with argon, stirred and heated at 105° C. for 5 hours. After all the reactant was reacted, 12.5 mg of product was collected by column chromatography with 7:3 hexanes:ethyl acetate as solvent. The mass of compound (4), as determined by mass spectrometry, was $[M^{+1}]=372.3$.

Scheme 1

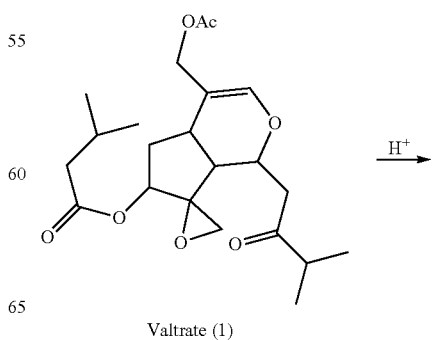

Valtrate (1)

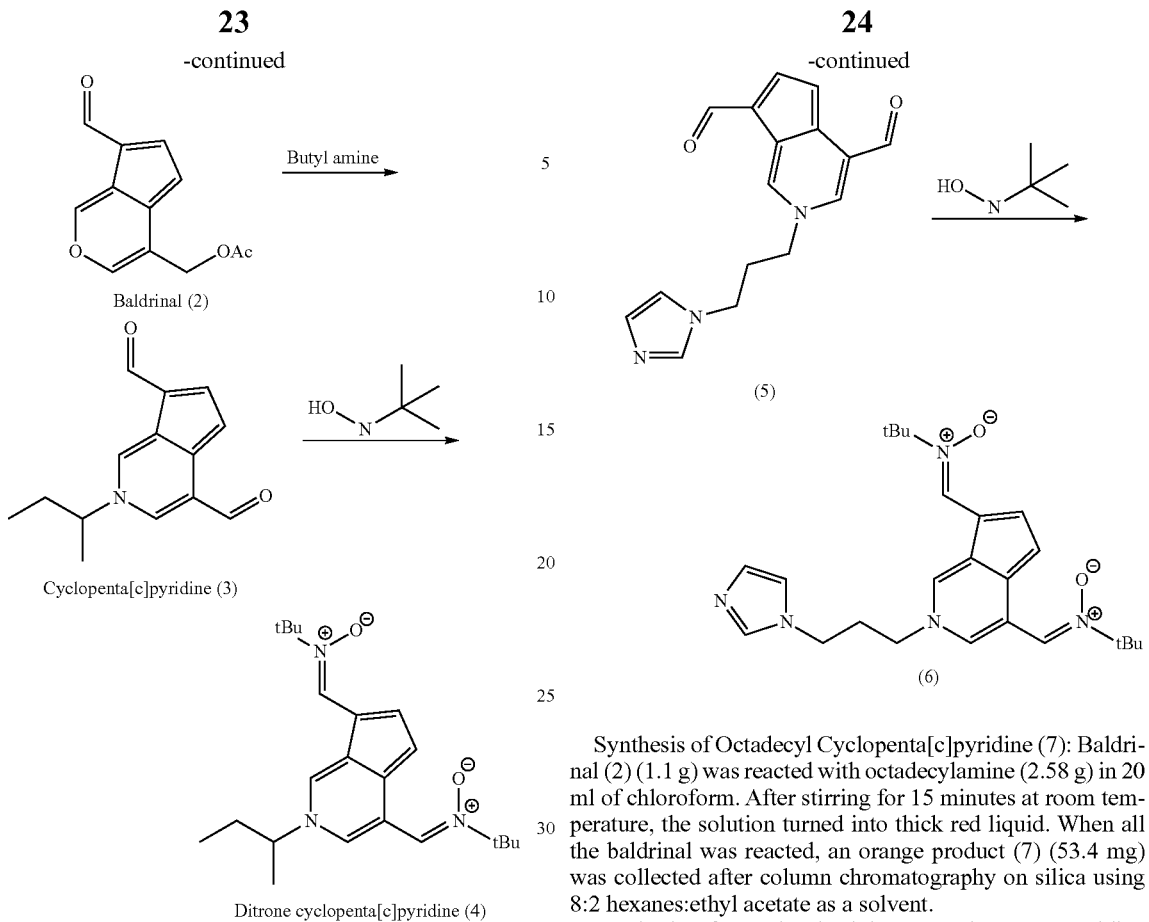

Baldrinal (2)

Cyclopenta[c]pyridine (3)

Ditrone cyclopenta[c]pyridine (4)

Synthesis of Imidazole Cyclopenta[c]pyridine (5): Baldrinal (2) (2.7 g) was reacted with 1-(3-aminopropyl)-imidazole (2.94 g) in 2 ml of chloroform. After stirring for 10 min at room temperature, no baldrinal was detected in the reaction mixture. Compound (5) was separated on column with silica using 20:1 CHCl$_3$:MeOH solvent system, and 26.7 mg of product was collected.

Synthesis of Imidazole Dinitrone cyclopenta[c]pyridine (6): Imidazole cyclopenta[c]pyridine (5) (12.6 mg) was mixed with N-tert-butyl hydroxylamine (22.5 mg) and MgSO$_4$ (22 mg) in 2 ml of pyridine. The flask was flushed with argon, stirred and heated at 60° C. for 20 hours. Once starting material was no longer detected, the product was extracted with CHCl$_3$/H$_2$O. Chloroform layer was collected and solvent evaporated. The product (9.1 mg) was collected after column chromatography on silica with 9:1 CHCl$_3$:MeOH as solvent.

Synthesis of Octadecyl Cyclopenta[c]pyridine (7): Baldrinal (2) (1.1 g) was reacted with octadecylamine (2.58 g) in 20 ml of chloroform. After stirring for 15 minutes at room temperature, the solution turned into thick red liquid. When all the baldrinal was reacted, an orange product (7) (53.4 mg) was collected after column chromatography on silica using 8:2 hexanes:ethyl acetate as a solvent.

Synthesis of Octadecyl Dinitrone cyclopenta[c]pyridine (8): Octadecyl cyclopenta[c]pyridine (7) (28 mg) was mixed with N-tert-butyl hydroxylamine (33 mg) and MgSO$_4$ (32 mg) in 2 ml of pyridine. The flask was flushed with argon, stirred and heated at 80° C. for 20 hours. After the starting material was no longer detected, the product was extracted with CHCl$_3$/H$_2$O. The chloroform layer was collected and solvent evaporated. After column chromatography with 20:1 CHCl$_3$:MeOH, the product (8) (15 mg) was collected.

Scheme 2

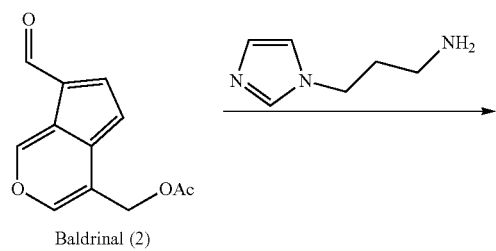

Baldrinal (2)

Scheme 3

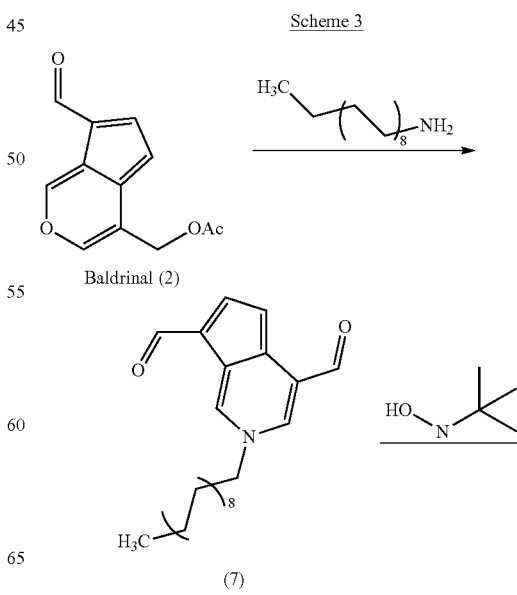

25
-continued

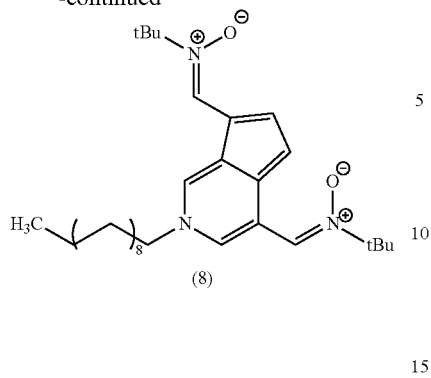

26
-continued

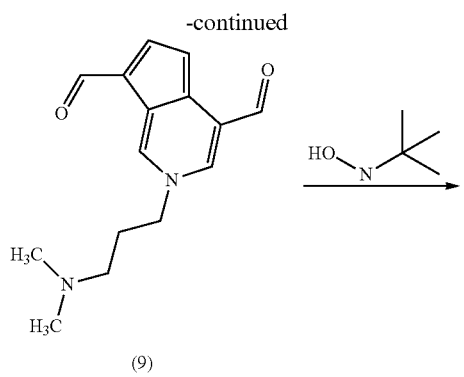

Synthesis of Cyclopenta[c]pyridine (9): Baldrinal (2) (12.8 mg) was reacted with 3-(dimethylamino)-1-propylamine (22.5 mg) in 2 ml of chloroform. After stirring for 10 minutes at room temperature, the solution turned red and all the baldrinal was reacted. Compound (9) was separated using column chromatography with silica using 50:1 CHCl$_3$:MeOH solvent system and 2.2 mg of product was collected.

Synthesis of Dinitrone cyclopenta[c]pyridine (10): Cyclopenta[c]pyridine (9, 34 mg) was mixed with N-tert-butyl hydroxylamine (66.1 mg) and MgSO$_4$ (63.3 mg) in 2.5 ml of pyridine. The flask was flushed with argon, stirred and heated at 60° C. for 20 hours. Once starting material was no longer detected, product was extracted with CHCl$_3$/H$_2$O. The organic layer was collected and solvent evaporated. A wine colored product (26.7 mg) was collected after column chromatography on silica with 20:1 CHCl$_3$:MeOH as solvent.

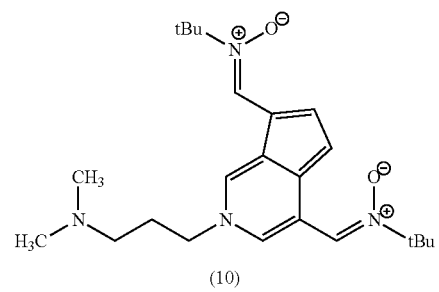

Synthesis of Quaternary Ammonium pyridines (12) and (14): Compound (10) is reacted with 1,4-diiodobutane to form a quaternary ammonium pyridine (11). Compound (II) then is reacted with N,N,N',N'-tetramethyl propylene-1,3-diamine to form quaternary ammonium pyridine (12).

Alternatively, compound (10) is reacted with 1,2-dimethylchlorobenzene to form a quaternary ammonium pyridine (13). Compound (13) then is reacted with N,N,N',N'-tetramethyl propylene-1,3-diamine to form quaternary ammonium pyridine (12).

Scheme 4

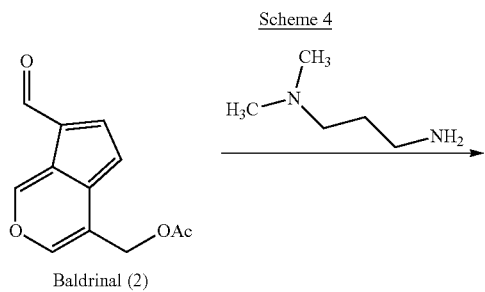

Scheme 5

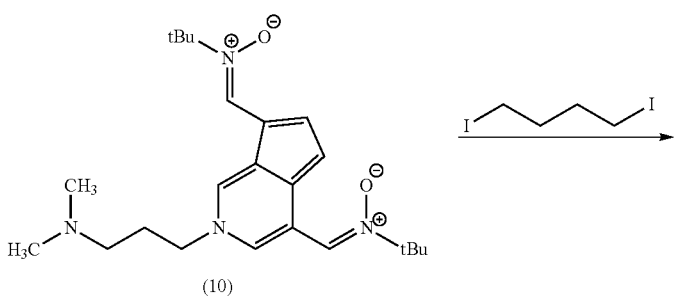

27 28
-continued
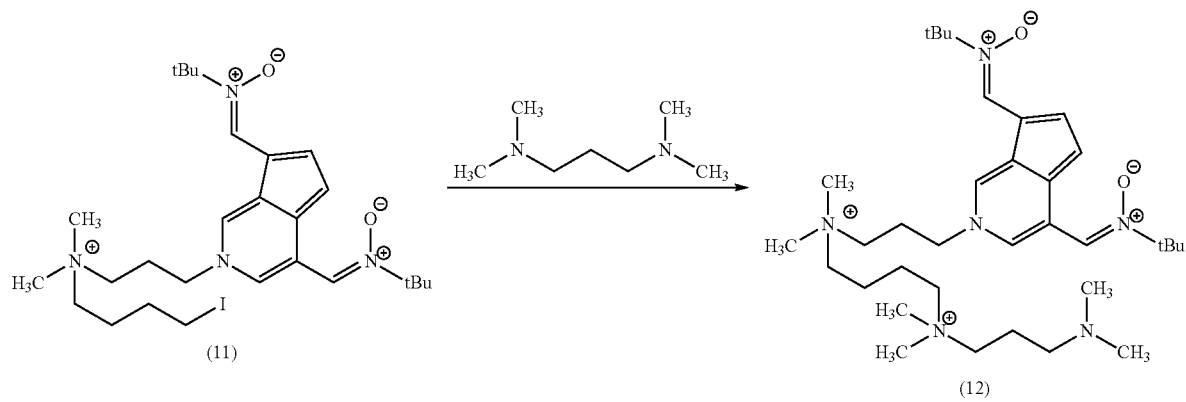
Scheme 6
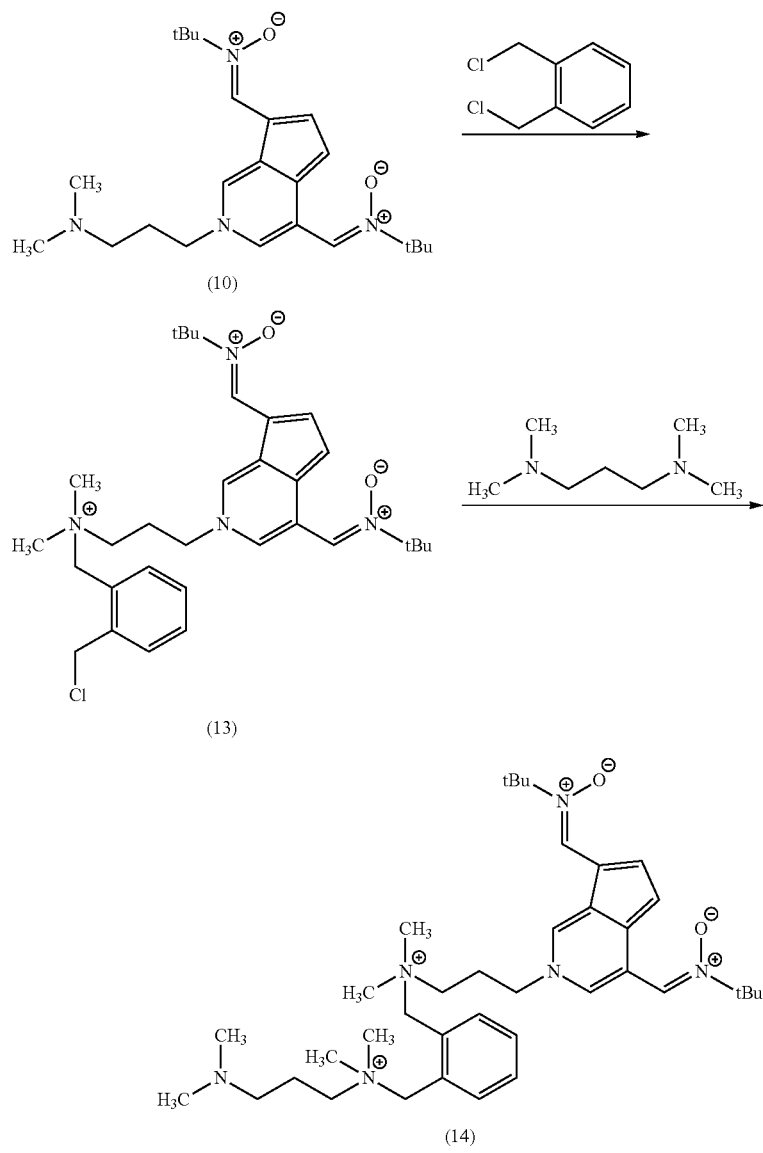

All of the above U.S. patents, U.S. patent application publications, U.S. patent applications, foreign patents, foreign patent applications and non patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A compound having a general structural formula (I) or formula (II):

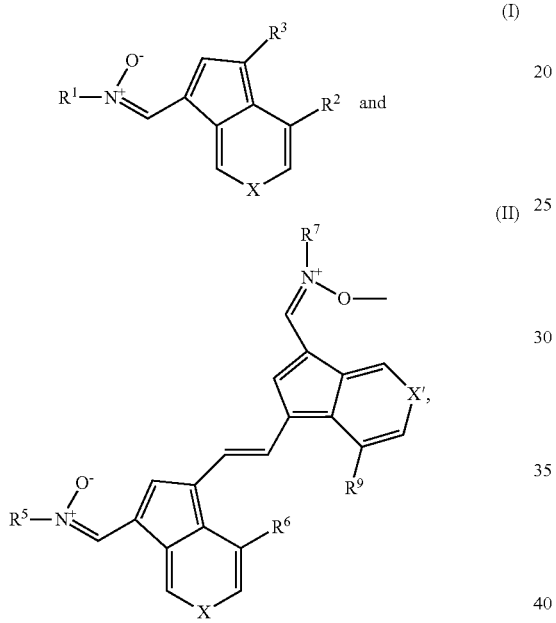

wherein $R^1$, $R^5$, and $R^7$ are the same or different and are independently selected from the group consisting of hydrogen, $C_{1-4}$ alkyl, phenyl, substituted phenyl, benzyl, substituted benzyl, tris(3-hydroxypropyl)methyl, (3-carboxy-1,1-dimethyl)propyl, and 3-sulfonatophenyl; $R^2$, $R^6$, and $R^9$ are the same or different and are selected from the group consisting of hydrogen, $C=C(H)N^+(R^1)O^-$, $C_{1-22}$alkyl, $C_{1-10}$alkyleneOC(O)C$_{1-10}$alkyl, and CHO; $R^3$ is selected from the group consisting of hydrogen, $C_{1-22}$alkyl, $SR^{12}$, and $SO_3^-$; X is selected from the group consisting of O, S, and $NR^4$; X' is selected from the group consisting of O, S, and $NR^8$; $R^4$ and $R^8$ are the same or different and are selected from the group consisting of hydrogen, $C_{1-22}$ alkyl, phenyl, substituted phenyl, $(C_{1-22}$alkyleneN$(R^{12})_2^+)_nC_{1-22}$alkyleneN$(R^{12})_2$, $C_{1-22}$alkyleneOR$^{11}$, $C_{1-22}$alkyleneP$(R^1)_3^+$, $C_{1-22}$alkylene aryl, $C_{1-22}$alkylene substituted aryl, $C_{1-22}$alkylene heteroaryl, and $C_{1-22}$alkylene substituted heteroaryl; $R^{10}$ is independently selected from the group consisting of hydrogen, $C_{1-10}$alkyl, $C_{1-10}$alkyleneN$(R^{12})_3^+$, and $C_{1-10}$alkylene-$C_6H_4$—$C_{1-10}$alkyleneN$(R^{12})_3^+$; $R^{11}$ is selected from the group consisting of hydrogen, $C_{1-10}$alkyl, $SO_2CF_3$, $SO_2CH_3$, $SO_2C_6H_4CH_3$, and $SO_2C_4F_9$; and $R^{12}$ is selected from the group consisting of hydrogen, $C_{1-22}$alkyl, aryl, heteroaryl, substituted aryl, and substituted heteroaryl; n is an integer from 0 to 3; or a pharmaceutically acceptable salt thereof.

2. The compound of claim 1, wherein X is $NR^4$; X' is $NR^8$, or X is $NR^4$ and X' is $NR^8$.

3. The compound of claim 1, wherein $R^2$ is $C=C(H)N^+(R^1)O^-$.

4. The compound of claim 1, wherein X is O or X' is O, or X and X' are each O.

5. The compound of claim 1 selected from the group consisting of:

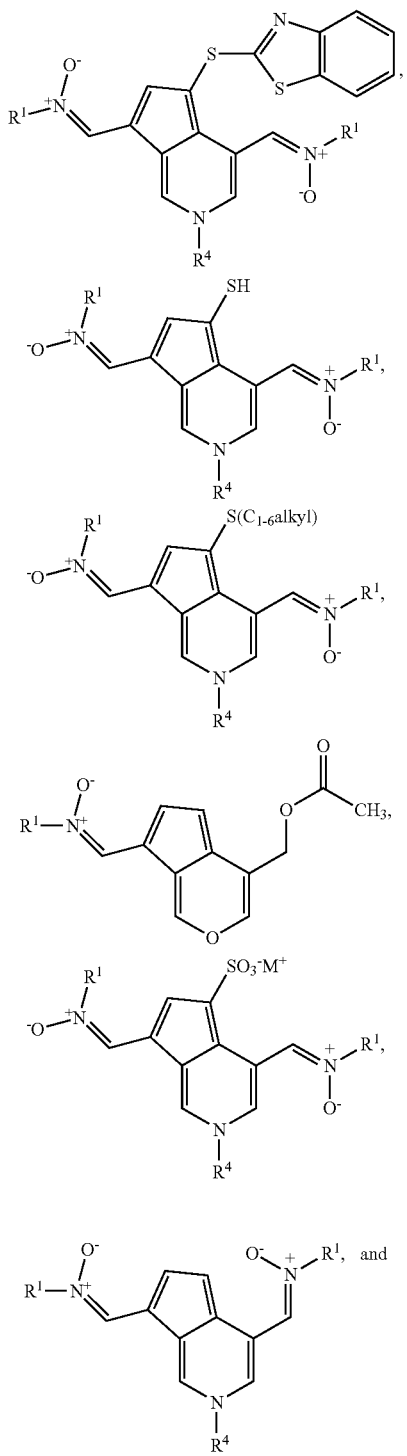

-continued

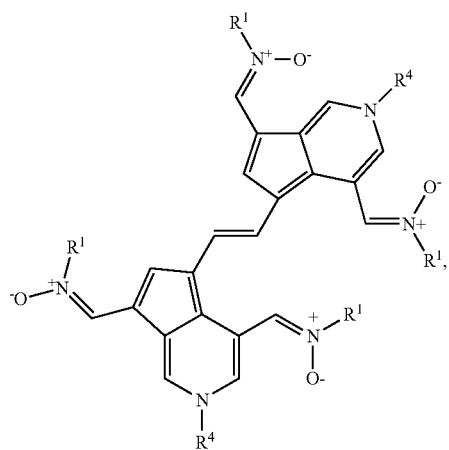

6. The compound of claim 1 selected from the group consisting

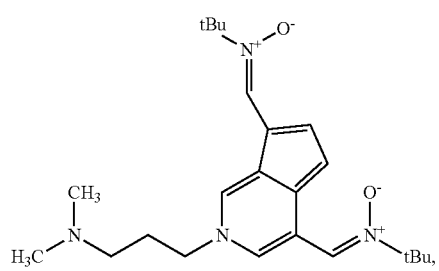

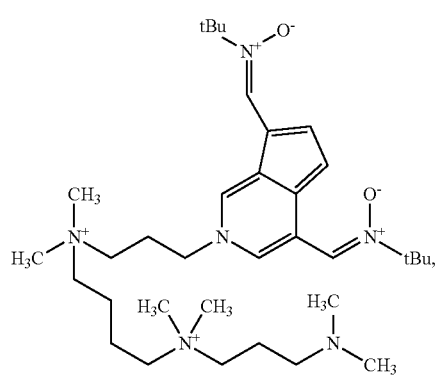

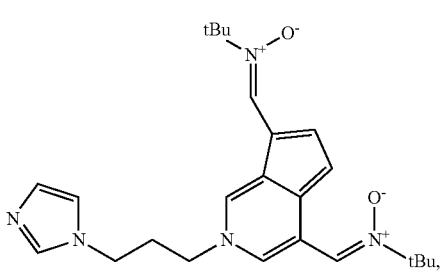

-continued

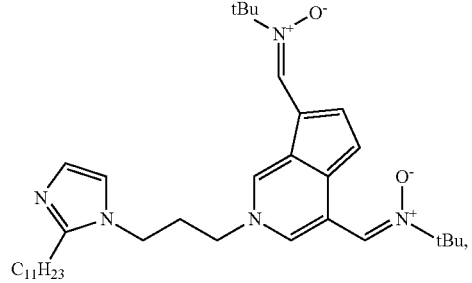

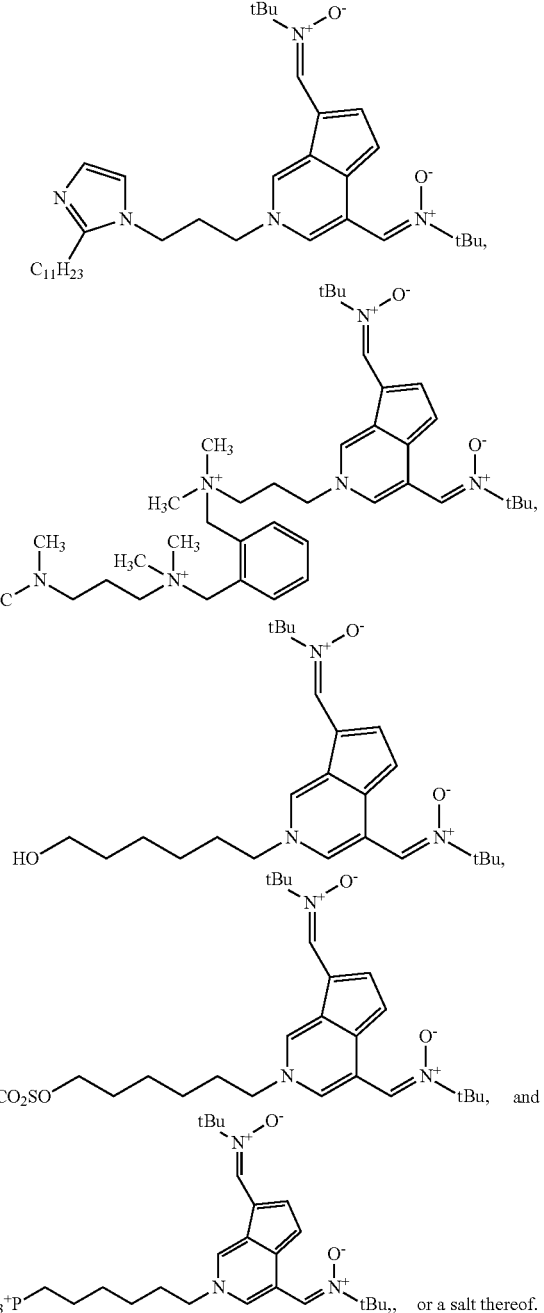

or a salt thereof.

wherein Ph is phenyl and tBu is tert-butyl.

7. A method of trapping a reactive free radical comprising contacting a compound of claim 1 with the reactive free radical to form an adduct of the compound and the reactive free radical.

8. A method of screening for free radicals comprising contacting a compound suspected of producing free radicals with a compound of claim 1 to form an adduct of the free radical and the compound of claim 1, and measuring a ratio of the adduct to the compound of claim 1, wherein a ratio greater than 0 indicates the presence of free radicals.

* * * * *